United States Patent [19]

Barrington

[11] 4,151,840

[45] May 1, 1979

[54] IMPLANTABLE PENILE PROSTHESIS

[75] Inventor: James E. Barrington, Woburn, Mass.

[73] Assignee: Abcor, Inc., Wilmington, Mass.

[21] Appl. No.: 872,915

[22] Filed: Jan. 27, 1978

[51] Int. Cl.$^2$ .............................................. A61F 5/00
[52] U.S. Cl. ..................................................... 128/79
[58] Field of Search .................................. 128/79; 3/1

[56] References Cited

U.S. PATENT DOCUMENTS

| | | | |
|---|---|---|---|
| 3,893,456 | 7/1975 | Small et al. | 128/79 |
| 3,987,789 | 10/1976 | Timm et al. | 128/79 |
| 4,066,073 | 1/1978 | Finney et al. | 128/79 |

*Primary Examiner*—Lawrence W. Trapp
*Attorney, Agent, or Firm*—Richard P. Crowley

[57] ABSTRACT

A mechanical penile prosthesis designed to be surgically implanted in the penis for the treatment of erectile impotence or as a functional component of a penile replacement prosthesis. The penile prosthesis comprises a pre-stretched, flexible, elastic, tubular component or sheath closed at each end thereof, and a plurality of cylindrically shaped segments or links, each having one or more convex ends and/or a concave end, enclosed within the tubular component. The pre-stretched tubular sheath maintains the segments in reference to one another, i.e. link-to-link contact, so that on straightening of the normally curved tubular enclosure a concave end of a segment mates with a convex end of an adjacent segment whereby the segments are aligned into a straight rod configuration resulting in an erect penis.

9 Claims, 6 Drawing Figures

IMPLANTABLE PENILE PROSTHESIS

BACKGROUND OF THE INVENTION (1) Field of The Invention

This invention relates to a mechanical penile prosthesis, to its manner of construction, and its use for the treatment of erectile impotence or as a functional component of a penile replacement prosthesis.

(2) Description of The Prior Art

Impotency is not only psychologically based, but can be related to nerve or vascular damage that may have been caused by severe diabetes, multiple sclerosis, spinal-cord injury or surgery in the lower abdomen, such as removal of bladder or for rectal cancer. It can also be the result of advanced age, trauma, and the side effects of drugs.

One surgical treatment for impotence involves, in particular, that caused by circulatory ills, revascularization, a technique developed by vascular surgeon Harry H. LeVeen of Brooklyn, New York. And while this technique has proved fairly simple, and apparently quite successful, it is limited to impotence that is caused by circulatory problems. Accordingly, it cannot be used to help patients with psychogenic or neurogenic impotence.

Another procedure that is being adopted more-and-more by surgeons for erectile impotence is penile prosthesis. This treatment is being used not only for impotence caused by age, disease, radical surgery, etc., but is also being used for psychogenic erectile impotence, but only after careful patient evaluation, generally when conventional sex therapy fails.

The modern era of penile implants is but five years old, spawned by development of two new, though very different, prostheses. One emphasizes simplicity, both of surgery and function, but gives the recipient a permanent erection. The other offers the patient a choice of flaccidity or erection but is costlier, more complex, and more prone to mechanical problems.

The simpler prosthesis was developed by Drs. Michael P. Small and Herman M. Carrion of the University of Miami School of Medicine. It consists of a rod-like device with a silicone sponge interior encased in a medical grade silicone exterior. It is implanted in pairs within the crura and the corpora cavernosa.

The more sophisticated prosthesis was introduced by Dr. F. Brantley Scott, Professor of Urology at Baylor College of Medicine in Houston. It is a totally implantable device using paired inflatable silicone cylinders within the corpora cavernosa connected to a hydraulic pumping device implanted in the patient's scrotum. The fluid reservoir for pumping pressure is placed behind the patient's rectus muscle.

In the impotent patient, the flow of blood to the penis' blood vessels is impaired. The increased flow is necessary for the tissue surrounding the vessels to expand and cause erection. A prosthesis, or artificial device, that causes erection is surgically inserted into the cavities of spongy tissue in the penis. It is these two cavities that normally fill with blood during erection.

With the inflatable device, an inert fluid takes the place of the blood supply. Two inflatable silicone tubes are inserted along the side of the penis' spongy tissue. The cylinders are attached by small tubes leading to a fluid-filled sac, which is implanted under the patient's lower abdominal muscles. By manipulating the small valves placed under the skin of the scrotum, the patient may fill or empty the penile cylinders with fluid, thus causing erection, also called tumescence, or detumescence.

The big advantage of the inflatable device, over the permanently hard silicone rods, is aesthetic—the patient does not have a permanent erection—but insertion of the device requires a more major operation, and there are more post-operative complications. The surgical insertion of an inflatable prosthesis, moreover, generally precludes the ability to have a normal, unaided erection, although this is not usually true with the non-inflatable device.

SUMMARY OF THE INVENTION

There is provided by my invention a relatively simple, mechanical penile prosthesis designed to be surgically implanted in the penis for the treatment of erectile impotence or as a functional component of a penile replacement prosthesis.

In its more basic aspects, the penile prosthesis, according to the invention, consists of a plurality of independent, cylindrically-shaped, rigid, segments or links, in end-to-end contact with one another, encased within a closed end, tubular sheath or component. The sheath is molded of an elastomeric material. When the sheath is straightened, its compressive elasticity causes the links to align themselves in a straight rod, resulting in an erect penis.

Although the invention can take various forms, it is important that each link be provided with a concave end and a convex end, and that the links be aligned within the sheath in such a manner that a convex end of one link mates with a concave end of an adjacent link and that the concave end of the one link mates with the convex end of another adjacent link.

In the preferred embodiment of the invention, the prosthesis comprises four links or segments, and each is provided with a convex end and a concave end of mating configuration, the mating ends thus functioning as a ball and socket joint. In the more preferred embodiment, the concave end of each link is provided with a detent for a protrusion provided on the convex end of the mating link. Thus, the prosthesis maintains its straight rod position until the link detents have been manually overridden and bent, after which it maintains the flaccid posture of the penis.

Quite advantageously, the mechanical penile prosthesis, according to my invention, provides an erect or flaccid penile posture at will. The erect posture is longitudinally incompressible and resists lateral flexure allowing the otherwise flaccid penis to engage in successful copulation.

The flaccid posture of the prosthesis allows the penis to rest in a manner that imitates the natural flaccid position of the penis.

BRIEF DESCRIPTION OF THE DRAWING

The invention will be better understood by referring to the drawings in which like numerals refer to like parts in the various views, and in which.

DETAILED DESCRIPTION OF THE INVENTION AND THE PREFERRED EMBODIMENTS

Figures 1A, 1B:
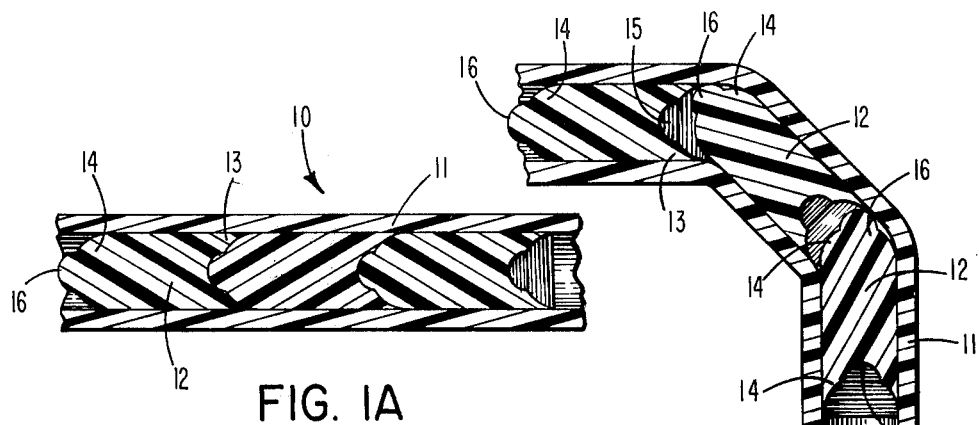
FIG. 1A is a sectional view down the center line of an implantable penile prosthesis in accordance with the invention disclosing the prosthesis in an erect position.
FIG. 1B shows the prosthesis in a flaccid position.

Turning now to the drawing, there is shown therein, in FIGS. 1A, 1B penile prosthesis 10, in accordance with the preferred embodiment of the invention, comprising a flexible, elastic, prestretched tubular component or sheath 11, in which are enclosed a plurality of independent, rigid, cylindrically-shaped links or segments 12, preferably four, each of which has a concave end 13, and a convex end 14, of mating configuration.

In the more preferred aspect of the invention, there is provided in concave end 13, a centrally located detent or depression 15, and on convex end 14, a centrally located protuberance 16. Protuberance 16 and indentation 15, as are concave end 13 and convex end 14, are preferably cylindrical with a semi-spherical end, and are located so that a radius of the sphere is located on the longitudinal center line of a segment. The radius and length of the indentation and protuberance will, of course, depend somewhat upon the diameter of the cylindrically-shaped segment or link 12. The main requirement is that protuberance 16 of one segment 12 mate with indentation 15 of an adjacent segment 12, so that the center line of both segments are in alignment with one another, when the prosthesis is in locked, erect position. However, the detent 15 obviously should not be overly deep, otherwise the pulling and bending force to override it will be excessive and could cause injury.

The segments can be molded of various relatively rigid materials, e.g. various plastic materials, for example, polycarbonate resin, polyacetal resin, polysulfone resin, etc. However, the more preferred is Lexan ® polycarbonate resin.

Although in FIG. 1A, 1B of the drawing, there is shown an indentation 15 in concave end 13 of segment 12, and protuberance 16 in convex end 14 thereof, it will be appreciated that instead of this particular configuration, a protuberance can be provided in the concave end, if desired, and a detent provided in the convex end.

Tubular component or sheath 11, while not specifically observable, as shown in FIG. 1B of the drawing, is in a normally straight configuration. And in this configuration, segments 12 are held in place with reference to their adjacent segments by the tubal sheath enclosure. However, as is seen in the drawing (FIG. 1B), the adjacent protuberances 16 are not engaged in depressions 15. Thus, the penile prosthesis, hence the penis when the prosthesis is implanted, may assume a normally flaccid position.

Tubular component 11, which must be of an elastomeric material and pre-stretched so as to be under tension, can be of various elastomeric, flexible materials. One such suitable material is a medical-grade silicone rubber.

In operation, an erection is produced simply by elevating by hand the otherwise flaccid penis containing the surgical implant, to the erect position. Elevation of the penis causes the sheath to straighten, automatically aligning the segments or links 12 of the penile prosthesis 10 and causing protuberance 16 in each link to engage with adjacent depression 15. When this occurs, a longitudinally, incompressible erection that resists lateral flexure results. Flexure is produced by pulling and physically bending the prosthesis manually which overrides the interfacial compression between adjacent segments at each protuberance and depression and effects flaccidity. Accordingly, an erect or flaccid penile posture can be assumed at will.

Figures 2A, 2B:
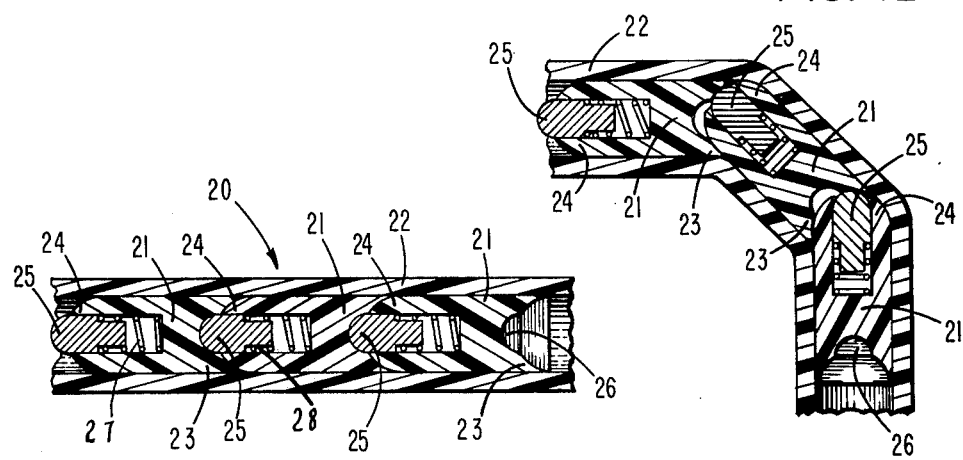
FIG. 2A shows a sectional view down the center line of another embodiment of an implantable penile prosthesis according to the invention showing the prosthesis in erect position.
FIG. 2B shows it in a flaccid position.

In FIGS. 2A, 2B of the drawing there is shown a further embodiment of a penile prosthesis 20 in accordance with my invention. Cylindrically-shaped segments 21 are enclosed in a tubular component 22 such as is shown in FIGS. 1A, 1B of the drawing, and in which the ends thereof are closed. Tubular component 22, as before described, can be of an elastomeric material and is in pre-stretched condition so as to maintain a compressive force upon segments 21, each of which has a concave end 23 and a convex end 24. Each segment or link 21, as is the case with segments 12, has a concave end 23 and a convex end 24 which engage with adjacent segments 21, as shown in the drawing. Recessed into the center of each convex end 24, is a spring-loaded protuberance 25, which protrudes sufficiently from the convex surface to engage a centrally located depression or detent 26, in a next adjacent segment 21, when the segments are longitudinally aligned in a straight rod configuration. (See FIG. 2A). The end of protuberance 25 that engages with spring 27 is desirably of cylindrical shape and of such a diameter that a portion 28 of protuberance 25 can intrude into the coil formed by the spring 27. Protuberance 25 engages with spring 27 so that protuberance 25 is placed under spring tension when adjacent segments or links 21 are axially aligned with one another.

The engagement of each spring-loaded protuberance 25 of a segment 21 with a depression 26 of an adjacent segment 21 results in the segments being longitudinally aligned in a straight rod configuration that resists flexure. Flexure can, however, be produced by physically bending the prosthesis manually, which overrides the spring-loaded protrusion detents and effects flexure.

In operation, as before described in connection with the prosthesis of FIGS. 1A, 1B, an erection is produced simply by elevating by hand the otherwise flaccid penis in which the prosthesis is implanted to the erect position. This elevation automatically aligns the segments 21 of the penile prosthesis 20 and engages the spring-loaded protuberances 25 with depression detents 26 so that a longitudinally incompressible erection is produced that resists lateral flexure.

Figure 3:
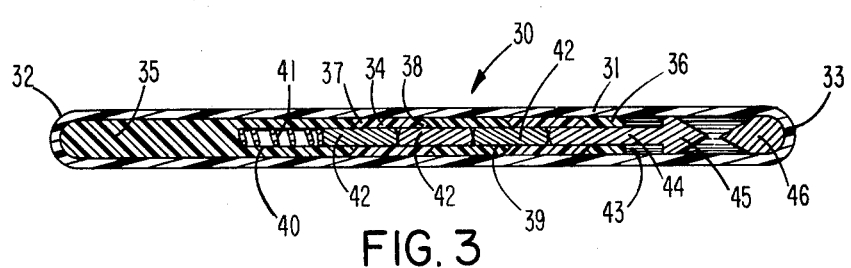
FIG. 3 is a sectional view down the center line of another embodiment of a penile prosthesis, according to the invention, showing the prosthesis in a rigid, erect position.

A further embodiment of a penile prosthesis, in accordance with the invention, is shown in FIG. 3 of the drawing. Therein, penile prosthesis 30 comprises a pre-stretched, elastic, tubular component 31, the ends 32, 33 of which, as shown in the drawing, are closed. A plurality of cylindrically-shaped, relatively rigid segments 34 are enclosed within the tubal sheath enclosure 31, which, as disclosed in the previous embodiments of the invention, maintains each segment 34 in place with reference to adjacent segments. This results from the fact that tubular component 31 is molded of an elastomeric material, and is in stretched condition. Each segment 34 intermediate the end segments 35, 36 has a concave end 37 and a convex end 38, and a longitudinal, cylindrical opening 39 down the center line thereof.

The anterior segment 35 has a blind hole 40 down its center containing a compression spring 41.

A plurality of solid rods 42, each of which has a length equal to the central axis length of a segment 34, is provided in each of the intermediate segments. These rods are of such a cylindrical dimension as to be able to slide back and forth within circular-shaped hole 39 and to protrude from one segment 34 into the hole in the next adjacent segment.

The posterior segment 36 of the penile prosthesis 30 is of slightly different configuration than the other segments, in that its one end 43 is flat rather than convex, the other end being concave to mate with a convex end 38. A cylindrical rod 44, having a conical end 45, is provided for axial movement, as shown by the directions of the arrow, through the center line hole in the posterior segment. In association with conical end 45 of segment 36, is an inverted conical member 46, located in the end of sheath 31, the purpose of which will be explained shortly, if not already obvious.

The compression spring 41 in anterior segment blind hole 40 is of such an uncompressed length that it pushes its rod 42 partially out of the longitudinal, blind hole in the end of the anterior segment and into the hole in the next adjacent segment 34. This action partially displaces the rod 42 in that segment, which in turn partially displaces the rod in the next segment, etc. This non-alignment of rod ends with segment ends locks the segments into a stiff rod configuration and produces an erect penile prosthesis, hence an erect penis when the prosthesis is implanted.

When the rod ends are manually aligned with the respective segment ends, they compress the lock spring 41 in the anterior segment 35 and the segments become unlocked. The penile prosthesis can then be bent to allow the penis to assume a flaccid posture. This is accomplished by squeezing the tapered portion of the two inverted conical segments 45, 46, conical segment 45 being the end portion of rod 44. In this way, lateral compression is translated into longitudinal force to compress the lock spring 41 and align the segments and their respective rods.

To erect the penis, one simply raises it to the erect position and the penile prosthesis 30 implanted therein will automatically lock in the erect position.

Figure 4:
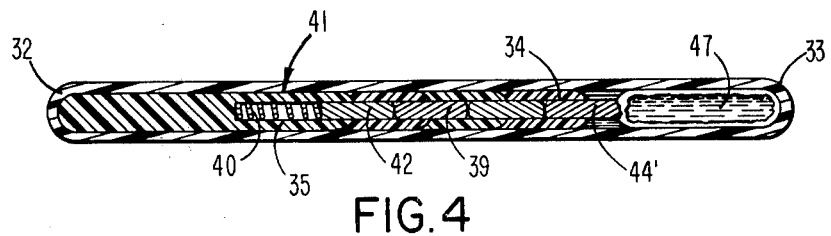
FIG. 4 is still a further embodiment of a sectional view taken down the center line of a penile prosthesis, according to the invention, showing the prosthesis in an erect position.

The lateral compression needed to cause movement of the rods 42 can be accomplished by a gas or liquid-filled elastomeric capsule, which increases its longitudinal dimension when its lateral dimension is manually compressed, rather than manually as shown in FIG. 3 of the drawing. Such an embodiment of the invention is shown in FIG. 4. Therein the posterior rod 44' is associated with a fluid-filled capsule 47. The implanted penile prosthesis 50 will assume the flaccid position when its fluid-filled capsule 47 is manually squeezed through the skin, and the penis is bent down to the desired position. To erect the penis, simply raise it to the erect position and the penile prosthesis will automatically lock in the erect position.

As many different embodiments of this invention will now occur to those skilled in the art, it is to be understood that the specific embodiments of the invention as presented herein are intended by way of illustration only and not limiting on the invention, but that the limitations thereon should be determined only from the appended claims.

What I claim is:

1. Penile prosthesis for the treatment of erectile impotence comprising a flexible, pre-stretched, elastic, tubular component closed at each end thereof, a plurality of independent, cylindrically-shaped, relatively rigid segments each segment having a convex end and a concave end, enclosed within said tubular component and being held in place with reference to adjacent segments by said tubular component so that on straightening of said normally curved tubular component a concave end of a segment mates with a convex end of an adjacent segment whereby an erection is produced in an otherwise normally flaccid penis and flexure is obtained by pulling and physically bending the prosthesis so as to disengage adjacent convex and concave ends.

2. Penile prosthesis for the treatment of erectile impotence according to claim 1 further comprising a protuberance from said convex end in each segment, and a depression in each concave end in each segment, whereby on elevation of the penis containing such an implant the curved tubular component is straightened and the tension of the pre-stretched tubular component aligns the segments of the penile prosthesis and engages the adjacent protuberances and depressions and maintains the segments under compression.

3. Penile prosthesis for the treatment of erectile impotence according to claim 2 wherein the segments comprise polycarbonate resin.

4. Penile prosthesis for the treatment of erectile impotence according to claim 1 wherein the flexible, pre-stretched tubular component comprises a polymeric material.

5. Penile prosthesis for the treatment of erectile impotence according to claim 4 wherein the polymeric material is a medical-grade silicone rubber.

6. Penile prosthesis for the treatment of erectile impotence according to claim 2 further comprising a compression spring associated with each protuberance, said compression spring being located in a cylindrical blind hole located axially inwardly from said convex end of each segment, whereby each protuberance is compressed on being associated with an adjacent depression.

7. Penile prosthesis for the treatment of erectile impotence according to claim 1 wherein a cylindrical blind hole is provided in the anterior segment in its end next adjacent intermediate segment, a cylindrical hole is provided down the center line in each intermediate segment from said concave end to said convex end, and a cylindrical rod is provided in each intermediate segment of such a length that from end to end it corresponds to the length of a segment from concave end to convex end, a compression spring in said blind hole for providing a force against an adjacent rod, and a means associated with the rod in the posterior segment to cause said rod to move and move said adjacent rod thereby providing a force to compress said spring and allow the rods to line up with their respective segments whereby the prosthesis can be placed in a flaccid posture.

8. Penile prosthesis for the treatment of erectile impotence according to claim 7 wherein the rod in the posterior segment is provided with a conically-shaped end, and the prosthesis further includes an inverted conical-shaped member associated with said conically-shaped rod end whereby on squeezing the tubal component at the location of the conically-shaped members, lateral compression is translated into a longitudinal force to compress the lock spring and align the segments and their respective rods.

9. Penile prosthesis for the treatment of erectile impotence according to claim 7 wherein the means associated with the rod in the posterior segment is a fluid-filled capsule.

* * * * *